US00PP08179P

United States Patent [19]

VandenBerg

[11] Patent Number: Plant 8,179

[45] Date of Patent: Mar. 16, 1993

[54] CHRYSANTHEMUM PLANT NAMED RAPTURE

[75] Inventor: Cornelis P. VandenBerg, Salinas, Calif.

[73] Assignee: Yoder Brothers, Inc., Barberton, Ohio

[21] Appl. No.: 743,095

[22] Filed: Aug. 9, 1991

[51] Int. Cl.[5] ..... A01H 5/00

[52] U.S. Cl. ..... Plt./74.1

[58] Field of Search ..... Plt./74.1, 82.5

*Primary Examiner*—Howard J. Locker

*Attorney, Agent, or Firm*—Foley & Lardner

[57] ABSTRACT

A Chrysanthemum plant named Rapture particularly characterized by its flat capitulum form; spoon daisy capitulum type; dark red-purple ray floret color; diameter across face of capitulum of 76 to 89 mm when fully opened, when grown as a pinched spray pot mum; and 89 to 102 mm when grown as a pinched disbudded pot mum; photoperiodic flowering response to short days of 48 to 56 days; plant height, with 15 to 18 long days after sticking unrooted cuttings, and with 1 application of 2500 ppm B-9 SP, ranges from 20 to 25 cm when grown as a pinched pot mum with 4 cuttings in a 15 cm pot; branching pattern is spreading and prolific, each plant having 5 to 6 laterals after pinch; and recommended as both disbud and spray pot mum.

3 Drawing Sheets

The present invention comprises a new and distinct cultivar of Chrysanthemum, botanically known as *Dendranthema grandiflora,* and referred to by the cultivar name Rapture.

Rapture, identified as 3239 (83-985013), was originated from a cross made by Cornelis P. VandenBerg in a controlled breeding program in Salinas, Calif., in 1983.

The female parent of Rapture was the cultivar identified as Chic, disclosed in U.S. Plant Pat. No. 5,660, and described as a daisy spray pot mum with a flat capitulum form; purple ray floret color; a diameter of capitulum of 5 to 7 cm; a flowering response period of 48 to 57 days after start of short days; a plant height ranging from 20 to 30 cm when grown as a pinched spray pot mum with 22 to 25 long days after sticking unrooted cuttings prior to start of short days and zero to three applications of 2500 ppm B-9 SP; and an upright branching pattern, each plant developing 3 to 5 laterals after pinch. Since filing for the U.S. plant patent for Chic in January 1984, the cultivar Chic has been treated extensively for many years, which accounts for a wider range for many characteristics in the above description for Chic when compared with the disclosure in U.S. Plant Pat. No. 5,660 for Chic.

The male parent of Rapture was an unnamed seedling identified as 1932 (79-U45004) and described as a spoon daisy spray pot mum with a flat capitulum form; light pink ray floret color; diameter of capitulum of 75 mm; flowering response period of 50 to 51 days after start of short days; plant height ranging from 20 to 30 cm when grown as a pinched pot mum with 14 to 19 long days after sticking unrooted cuttings prior to start of short days and one to three applications of 2500 ppm B-9 SP; and a spreading branching pattern, each plant developing 4 to 5 laterals after pinch. The male parent was discarded from all programs in February 1985.

Rapture was discovered and selected as one flowering plant within the progeny of the stated cross by Cornelis P. VandenBerg in June 1984, in a controlled environment in Salinas, Calif.

The first act of asexual reproduction of Rapture was accomplished when vegetative cuttings were taken from the initial selection in July 1984 in a controlled environment in Salinas, Calif., by technicians working under supervision of Cornelis P. VandenBerg.

Horticultural examination of controlled flowerings of successive plantings has shown that the unique combination of characteristics as herein disclosed for Rapture are firmly fixed and are retained through successive generations of asexual reproduction.

Rapture has not been observed under all possible environmental conditions. The phenotype may vary somewhat with variations in environment such as temperature, light intensity and daylength, without, however, any variance in the genotype.

The following observations, measurements and comparisons describe plants grown in Salinas, Calif. under greenhouse conditions which approximate those generally used in commercial greenhouse practice.

The following traits have been repeatedly observed and are determined to be basic characteristics of Rapture, which, in combination, distinguish this Chrysanthemum as a new and distinct cultivar.

1. Flat capitulum form.
2. Spoon daisy capitulum type.
3. Dark red-purple ray floret color.
4. Diameter across face of capitulum of 76 to 89 mm when fully opened, when grown as a pinched spray pot mum, and of 89 to 102 mm when grown as a pinched disbudded pot mum.
5. Photoperiodic flowering response of 48 to 56 days after start of short days.
6. Plant height with 15 to 18 long days after sticking unrooted cuttings, and with 1 application of 2500 ppm B-9 SP, ranges from 20 to 25 cm when grown as a pinched pot mum with 4 cuttings in a 15 cm pot.
7. Branching pattern is spreading and prolific, each plant having 5 to 6 laterals after pinch.
8. Recommended as both disbud and spray pot mum.

The accompanying photographic drawings show typical inflorescence and leaf characteristics of Rapture, with the colors being as nearly true as possible with illustrations of this type.

Sheet 1 is a color photograph of Rapture grown as a pinched disbudded potted mum with 4 cuttings in a 15 cm pot.

Sheet 2 is a black and white photograph of three views of the inflorescence of Rapture.

Sheet 3 is a black and white photograph showing the upper and lower sides of the leaves of Rapture at 3 stages of development (mature, intermediate and immature).

In sheets 2 and 3 a measuring tape in centimeters has been added.

Of the commercial cultivars known to the inventor, the most similar in comparison to Rapture is the cultivar identified as Pasadena, disclosed in U.S. Plant Pat. No. 7,346. Reference is made to attached Chart A, which compares certain characteristics of Rapture to the same characteristics of Pasadena.

Similar traits are capitulum form and type. Rapture has a larger spoon portion of the ray floret than Pasadena, and a better branching pattern. Although the branching pattern is spreading for both Rapture and Pasadena, Rapture develops an average of one more lateral after pinch then Pasadena. Ray floret color is similar, described as dark red-purple, but the color of Rapture is R.H.S. 61A, and Pasadena R.H.S. 59B. Rapture has a smaller diameter of capitulum and a slower flowering response to short days than Pasadena. In addition, Rapture is recommended as both disbud and spray pot mum, while Pasadena is recommended as disbud pot mum only. Rapture has more vigor than Pasadena, Rapture normally being grown with 15 to 18 long days after sticking unrooted cuttings prior to start of short days, while Pasadena requires 22 to 25 long days after sticking unrooted cuttings to acquire commercially desired plant height.

When compared with both parents, Rapture has a larger diameter of capitulum than both parents, and is recommended as both disbud and spray pot mum, while both parents are grown only as spray pot mums. Rapture develops an average of one more lateral after pinch than either parent.

In the following description color references are made to The Royal Horticultural Society Colour Chart. The color values were determined on plant material grown as a pinched disbudded pot mum in Salinas, Calif. on Apr. 9, 1991.

Classification:

*Botanical.*—*Dendranthema grandiflora* cv. Rapture.

*Commercial.*—Spoon daisy disbud and spray pot mum.

INFLORESCENCE

A. Capitulum:

*Form.*—Flat.

*Type.*—Spoon daisy.

*Diameter across face.*—89 to 102 mm when fully opened, when grown as a pinched disbudded pot mum.

B. Corolla of ray Florets:

*Color (general tonality from a distance of three meters).*—Dark red-purple.

*Color of spoon tips.*—61A.

*Color of tubes.*—70A to 70B.

*Shape.*—Spooned, with irregular length of spoons (See photograph).

C. Corolla of disc florets:

*Color (mature).*—9A.

*Color (immature).*—144A to 144B.

D. Reproductive organs:

*Androecium.*—Present on disc florets only; no pollen.

*Gynoecium.*—Present on both ray and disc florets.

PLANT

A. General appearance:

*Height.*—20 to 25 cm when grown as a pinched pot mum in a 15 cm pot with 15 to 18 long days after sticking unrooted cuttings and 1 application of 2500 ppm B-9 SP.

*Branching pattern.*—Spreading and prolific, with 5 to 6 laterals after pinch.

B. Foliage:

*Color (upper surface).*—147A.

*Color (under surface).*—147B.

*Shape.*—See photograph.

CHART A

| CULTIVAR | RAPTURE | PASADENA |
|---|---|---|
| Ray floret color | Dark red-purple | Dark red-purple |
| Capitulum form and type | Flat spoon daisy | Flat spoon daisy |
| Diameter across face of capitulum, disbudded | 89 to 102 mm | 127 to 159 mm |
| Flowering response | 48 to 56 days | 44 to 51 days |
| Branching pattern | Spreading 5 to 6 laterals | spreading 4 to 5 laterals |
| Recommended as | Disbud and spray | Disbud |

COMPARISONS MADE OF PLANTS GROWN AS PINCHED DISBUDDED POT MUMS IN SALINAS, CALIFORNIA

I claim:

1. A new and distinct Chrysanthemum plant named Rapture, as described and illustrated.

* * * * *

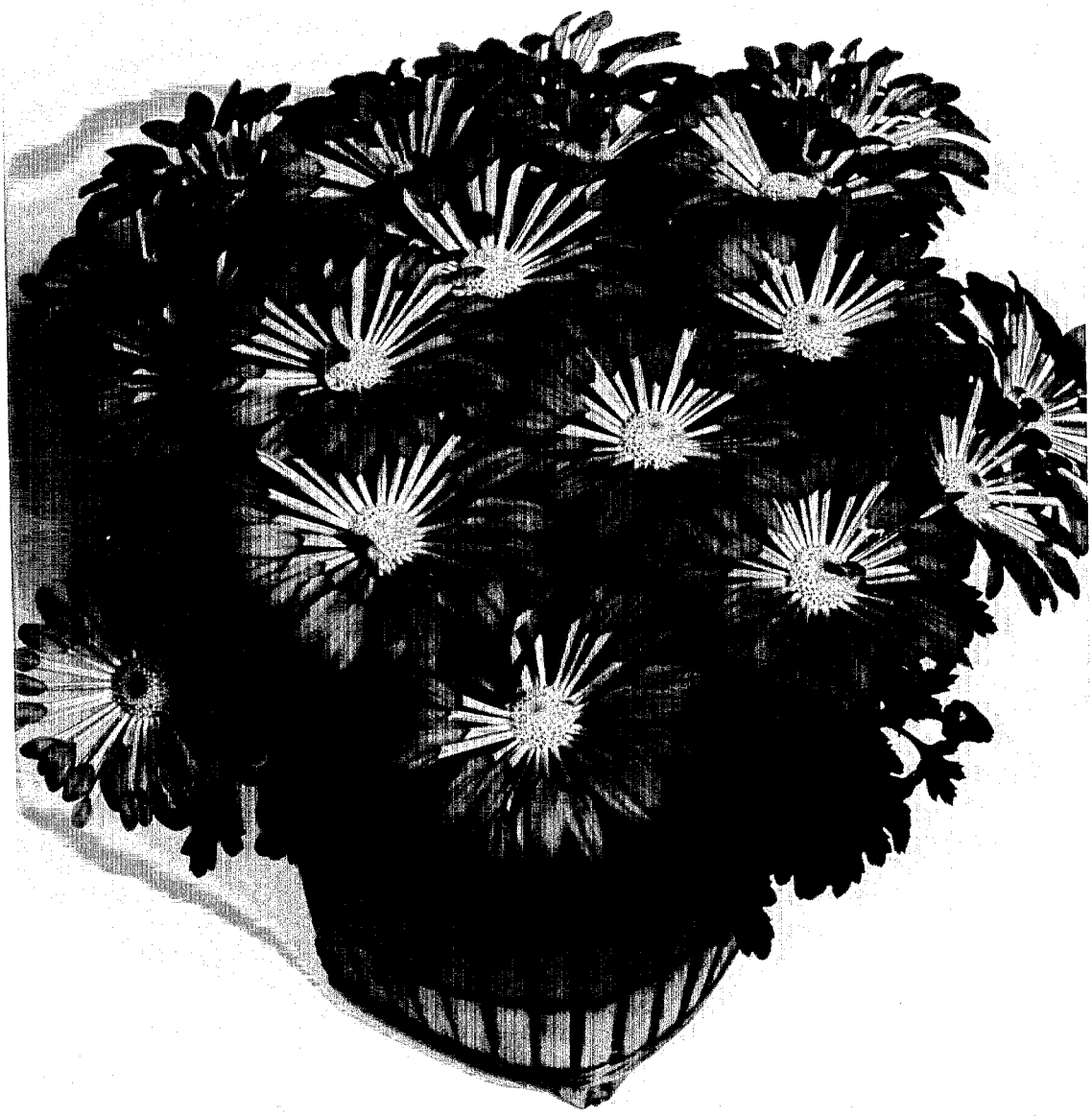

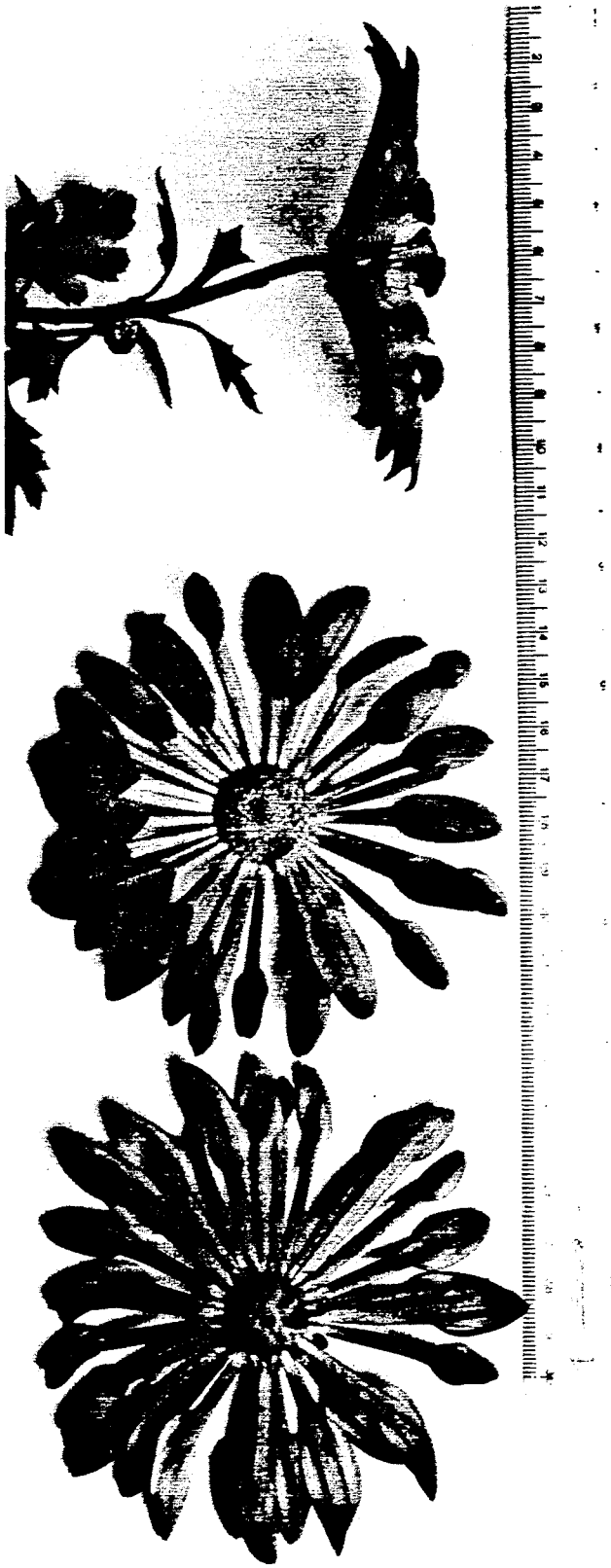

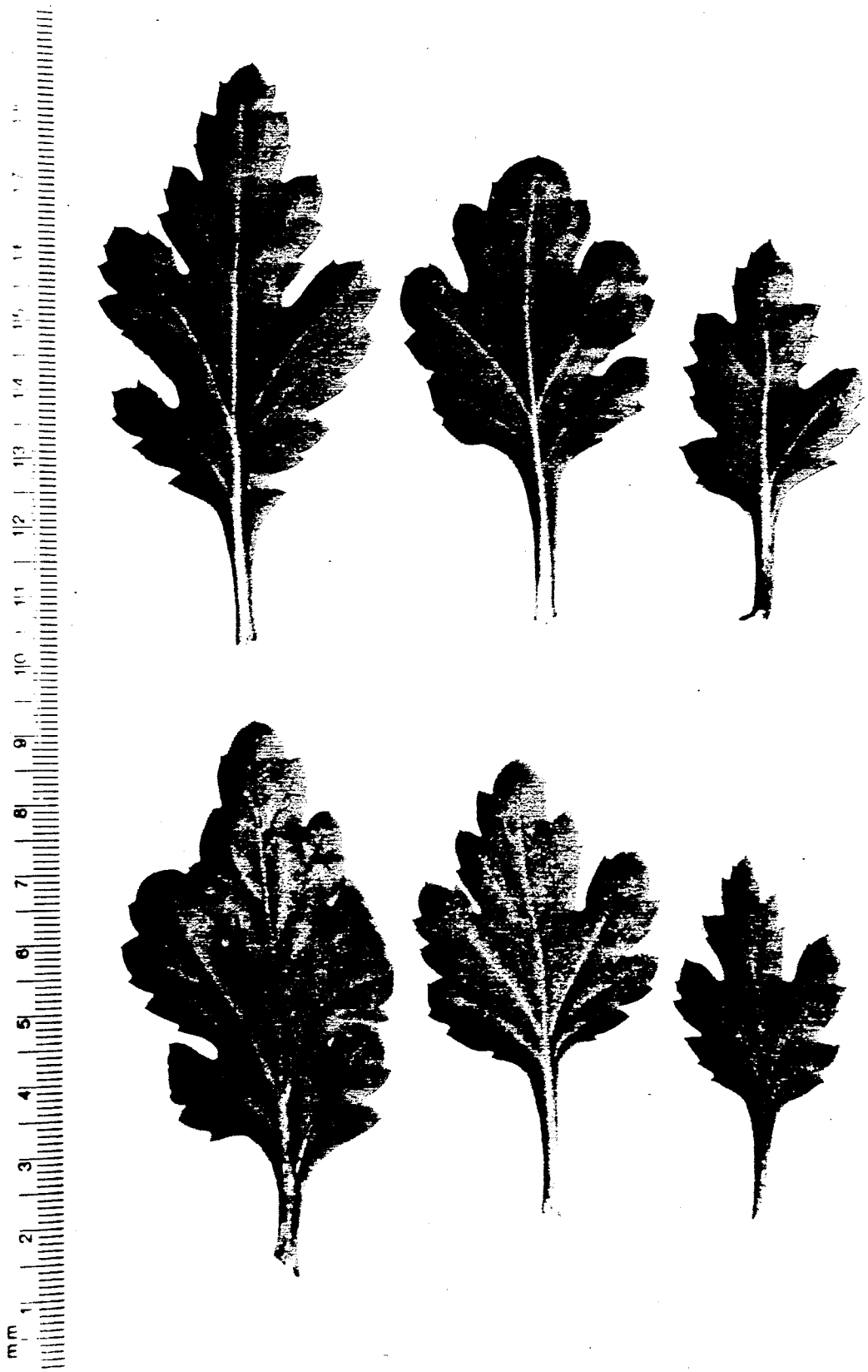
mm
1
2
3
4
5
6
7
8
9
10
11
12
13
14